United States Patent [19]

Baker

[11] Patent Number: 4,780,182

[45] Date of Patent: Oct. 25, 1988

[54] CONTINUOUSLY MONITORED APPARATUS AND METHOD FOR DETERMINING DEGREE OF COMPLETION OF PULP COOK

[75] Inventor: Clifford Baker, New London, Wis.

[73] Assignee: Paper Valley Instruments, Inc., Neenah, Wis.

[21] Appl. No.: 33,594

[22] Filed: Apr. 1, 1987

[51] Int. Cl.⁴ .................. D21C 7/12; G01N 21/00
[52] U.S. Cl. .................... 162/49; 73/61 R; 162/238; 162/258; 162/263; 422/62; 422/68; 436/52; 356/410
[58] Field of Search .............. 162/49, 258, 238, 61, 162/198, 263, DIG. 10; 73/61 R, 63, 53, 61.1 R; 422/62, 68; 436/52; 356/436, 410, 411

[56] References Cited

U.S. PATENT DOCUMENTS

| | | | |
|---|---|---|---|
| 3,838,594 | 10/1974 | Kesler | 162/263 |
| 4,192,708 | 3/1980 | Bergstrom et al. | 162/49 |
| 4,345,913 | 8/1982 | Jönsson | 162/49 |
| 4,540,468 | 9/1985 | Genco et al. | 162/49 |

Primary Examiner—Steve Alvo
Attorney, Agent, or Firm—James E. Nilles

[57] ABSTRACT

A method and suitable apparatus for periodically analyzing pulp stock, including wood pulp and water, in a pulp digester, to determine the amount of cooking to which the pulp has been subjected. The method includes taking a sample of the pulp stock from the digester, diluting the sample to a predetermined range of consistency, and determining the exact consistency of the sample. Next, the sample is transferred to a reaction chamber. A reagent is then added to the sample and allowed to react with the sample at a predetermined temperature. The light absorbance of the reagent during the reaction is continuously monitored during the reaction. After the light absorbance has clearly passed a peak, the value of the peak is combined with the consistency of the sample, previously determined, to arrive at the amount of cooking to which the sample had been subjected prior to the test, from a known relationship thereof to the light absorbance of the reagent and the consistency of the sample.

7 Claims, 6 Drawing Sheets

CONTINUOUSLY MONITORED APPARATUS AND METHOD FOR DETERMINING DEGREE OF COMPLETION OF PULP COOK

BACKGROUND OF THE INVENTION

This invention relates to methods and apparatus for determining certain properties of pulp, generally in a digesting or delignification reaction. More particularly, the invention relates to the testing of pulp under controlled and easily reproduced conditions to determine certain properties of the pulp, such as the amount of lignin a particular sample contains.

The sequence of operations in the chemical manufacture of wood pulp preparatory to the production of paper includes debarking of the wood, chipping or fragmenting of the wood, pulping of the chipped wood, and subsequent bleaching, washing, cleaning and screening of the pulp. Although the pulping step is fundamental to the production of paper, the pulping reaction itself is not completely understood. Commonly used chemical pulping processes include the sulfite process and the kraft (or basic) process. While the kraft process is the dominant process practiced industrially, accounting for approximately three-fourths of the total pulp production, fine and writing papers are generally produced using the sulfite process. Both processes are conducted by both batch and continuous methods.

Generaly, the control of either pulping process has been accomplished by means of an open loop, feed forward system. According to the most common method, the initial charge conditions such as chip moisture content, sulfidity, liquor to wood ratio, and acidity or alkalinity are monitored. Cooking over a given time and at a given temperature for particular values of these conditions is expected to result in the same pulp yield and Kappa number, or lignin content. The cook is then stopped at a time which is expected to give an acceptable pulp yield. Hence this conventional method is used to predict when to stop the cook in order to achieve a desired pulp yield. Upon stopping the cook, the pulp is analyzed to ascertain whether the desired degree of completion has in fact been attained. The results of this analysis are used to adjust the cooking parameters to be used on subsequent cooks, although if the current batch is not properly cooked, there is nothing further done to the pulp to bring it to the proper level of cook. Generally it is just used to manufacture a different type of paper than was intended.

One clear disadvantage of this conventional method is that control of the product of the pulping operation is dependent upon the maintenance of uniform input conditions of the cook, relating to ingredients such as chip moisture content, temperature and chemical properties. It is very difficult to accurately ascertain certain of these variables, such as chip moisture, in any practical way. Accordingly the results of one reaction are used to correct the conditions for the next run in a trial and error operation based on the questionable assumption that the average properties of the components remain substantially uniform from one cook to the next. Thus it has not been possible to close the open control loop of the conventional method because of the lack of suitable measurements obtainable in process.

Another approach to controlling the completeness of the pulp delignification process has been the method of measuring the "Kappa number", which is defined by the Technical Association of the Pulp and Paper Industry (TAPPI) standard T-236. The known relationship between the Kappa number and the lignin content is as follows: the percent lignin in the pulp equals 0.147 times the Kappa number. The Kappa number method, however, is not suitable for on-line measurement because the pulping reaction must be terminated and the pulp oven-dried in order to measure the Kappa number. Certain models have been developed over time to aid in inferring the Kappa number from measurement of other parameters, such as the measurement of sulfidity of the liquor by a selective ion electrode, or the titration of a liquor sample by acid. These methods have not received wide use within the industry. Virtually all of the pulping control done in this country employs the conventional method described above or equivalent feed forward control.

The patent issued to Pottenger, U.S. Pat. No. 3,674,434, teaches a system for determining the lignin content "directly", by measuring the ratio of elemental carbon to elemental hydrogen in a sample. Since this method requires termination of the reaction for direct sampling of the pulp, it is unsuited for online real time monitoring and process control.

The patent issued to Andrews, Jr., et al., U.S. Pat. No. 4,193,840, teaches a method for determining the degree of delignification by monitoring a combination of temperature and pressure. Because these parameters are only indirectly related to the lignin content of the pulp, reliability of the measurements is suspect.

The patent issued to Chase, et al., U.S. Pat. No. 4,162,933, determines the degree of delignification by monitoring heat given off by the chemical reaction of the digesting operation. Once again, the information taken is only indirectly related to the lignin content of the pulp, and so the reliability required for an on-line process control system is unavailable.

The Institute of Paper Chemistry (IPC) has disclosed a technique using the carbohydrate fraction of pulp to predict yield in continuous digesters. The method assumes that the yield of cellulose as a percentage of a particular wood species is substantially constant during a Kraft reaction. The method requires extremely accurate determination of pulp carbohydrates, such as by gas chromatography, thus being too expensive to be widely applicable to on-line real time measurement of pulp yield.

Finally, yet another apparatus and method for determining the degree of pulp cook of a sample are disclosed in U.S. patent application Ser. No. 944,201, filed Dec. 22, 1986, which was invented by the same inventor as the present application and assigned to the same assignee. In that apparatus and method, however, the test for consistency and the chemical reaction are conducted in the same chamber. Further, no provision is made to monitor the progress of the reaction, resulting in the failure to eliminate trial and error from the testing process.

This invention relates to improvements over the methods and apparatus described above and to solutions to the problems raised thereby.

SUMMARY OF THE INVENTION

The invention includes a method and suitable apparatus for periodically analyzing pulp stock, including wood pulp and water, from a pulp digester, to determine the amount of cooking to which the pulp has been subjected. The method includes taking a sample of the pulp stock from the digester, diluting the sample to a predetermined range of consistency, and determining the exact consistency of the sample. Next the sample is moved to another chamber where a reagent is added to the sample and allowed to react with the sample for a predetermined time interval at a predetermined temperature. Throughout the reaction, the color and clarity of the reagent is monitored, such as by circulating it through a flow cell colorimeter, to determine the exact point in the reaction at which the maximum light absorbance of the reagent is reached. The value of this maximum, in combination with the consistency already determined, indicates the amount of cooking to which the pulp has been subjected, by means of a known relationship.

It is thus an object of the invention to provide a method and apparatus for determining the degree of completion of cook of a pulp sample from a digester.

A more specific object of the invention is to provide a method and apparatus as described above including automatically determining the consistency of the pulp, adding a reagent to the pulp, and allowing the reagent to react with the pulp at a predetermined temperature for a predetermined time interval, while continuously monitoring the progress of the reaction to determine the peak light absorbance of the reagent.

Another specific object of the invention is to provide a method and apparatus as set forth above wherein the value of the peak light absorbance combines in a known relationship with the consistency to give a reference number in a standard scale determining the amount of cooking to which the pulp has been subjected.

Yet another object of the invention is to provide separate chambers for testing the consistency of the sample and for conducting the chemical reaction, to allow the two tests to be carried on concurrently, thereby increasing the efficiency of the apparatus.

Other objects and advantages of the invention will become apparent hereinafter.

DESCRIPTION OF THE PREFERRED EMBODIMENTS

Referring now to FIGS. 1, 2A, 2B and 2C, there is shown an apparatus 10, constructed according to a preferred embodiment of the inventon, for testing to determine the amount of cook to which a sample of pulp has been subjected. It should be understood that the various filling, draining and air movement operations disclosed below are controlled by suitable valves as is well known in the art. Hence these valves are not necessarily referenced individually. They may be controlled by any suitable control means, whether electronic, mechanical, or even by a human operator although in general completely automatic operation will be preferable so as to yield as much reproducibility in the testing as possible. Those valves which are not referenced individually may have relevance to facilitating the installation or maintenance of the system between test cycles, for instance.

Figure 1:
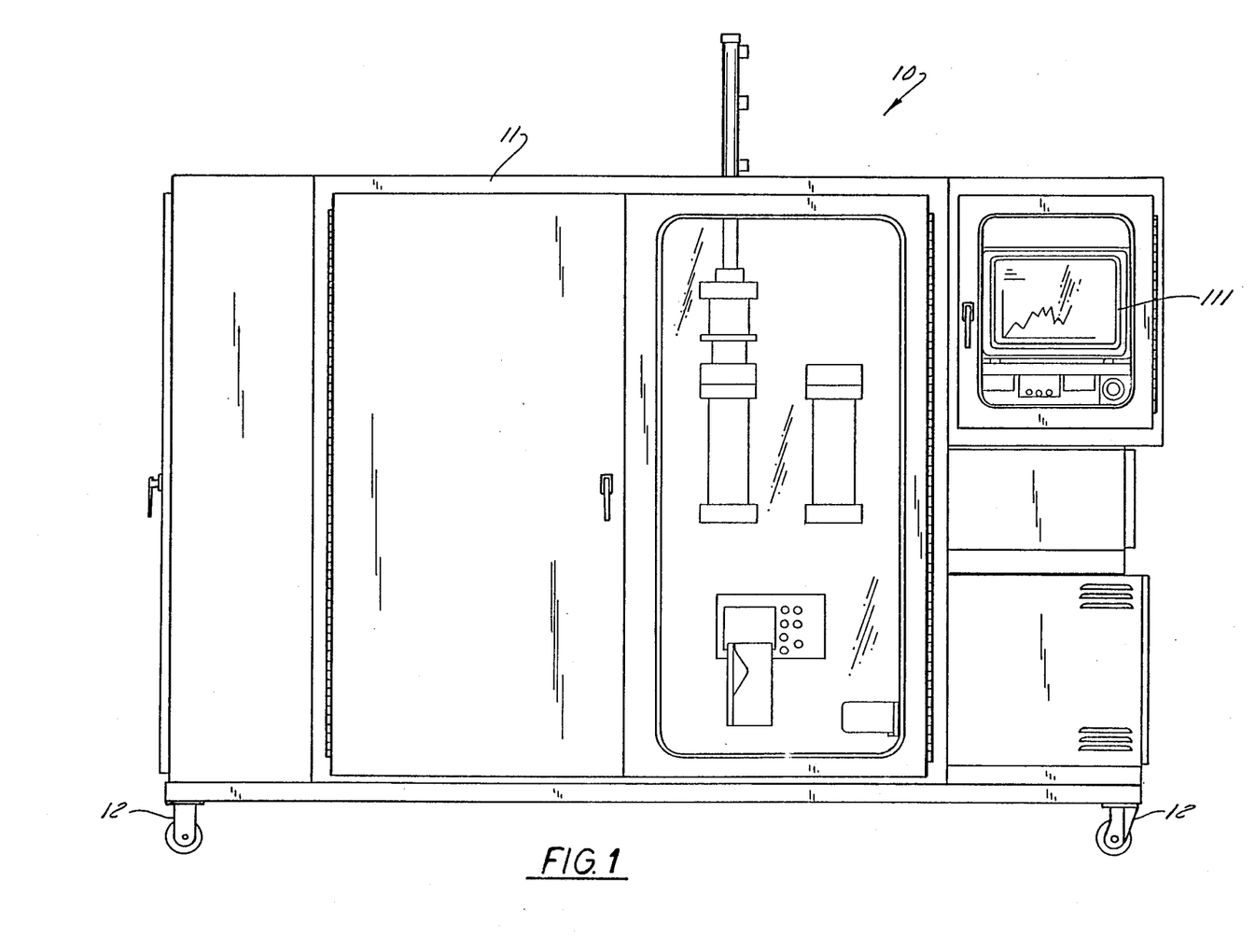
FIG. 1 is a front elevation view of an apparatus constructed according to one embodiment of the invention.
Figure 2A:
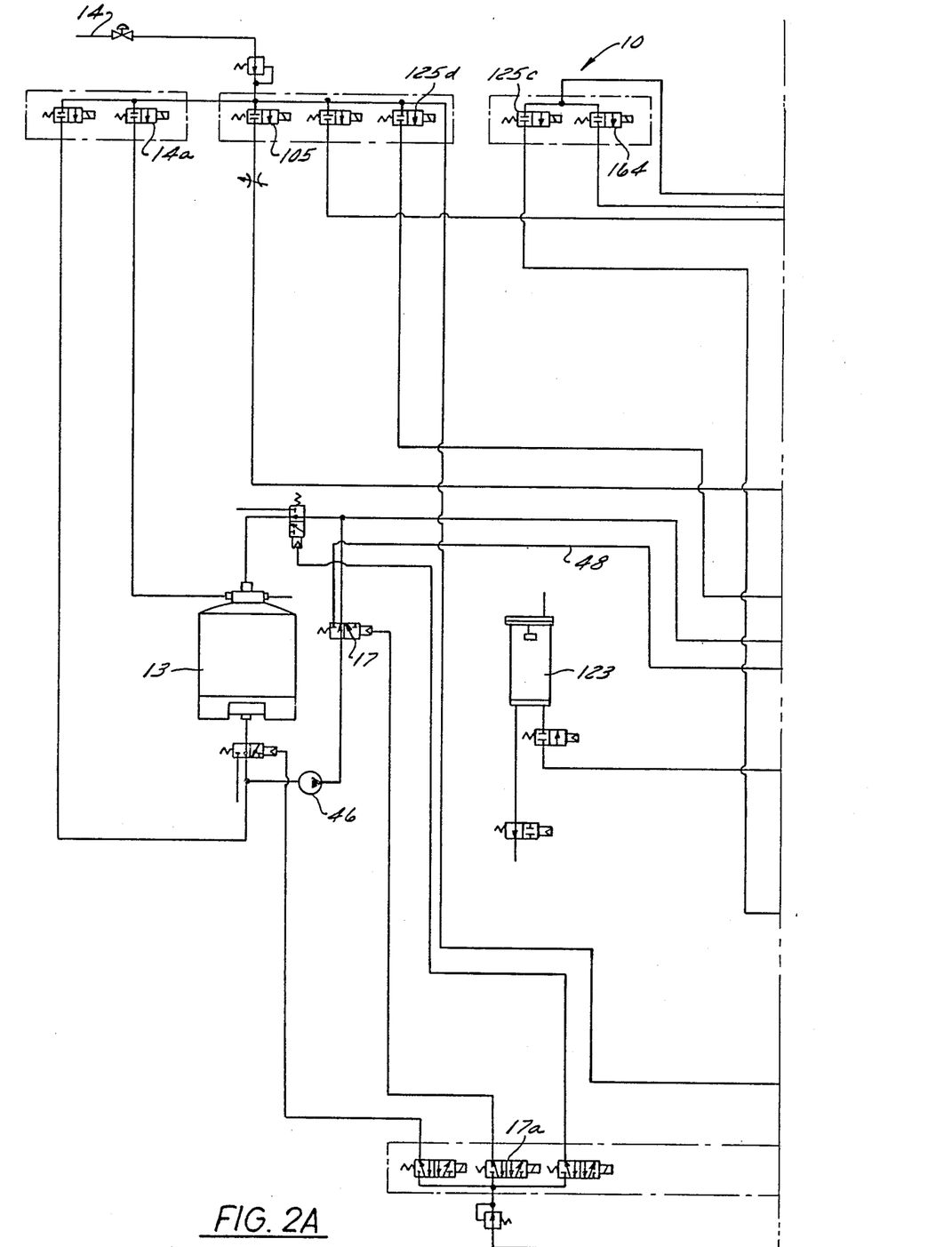
FIGS. 2A, 2B and 2C are the three parts of a schematic diagram of an apparatus assembled according to the embodiment of the invention shown in FIG. 1.
Figure 2B:
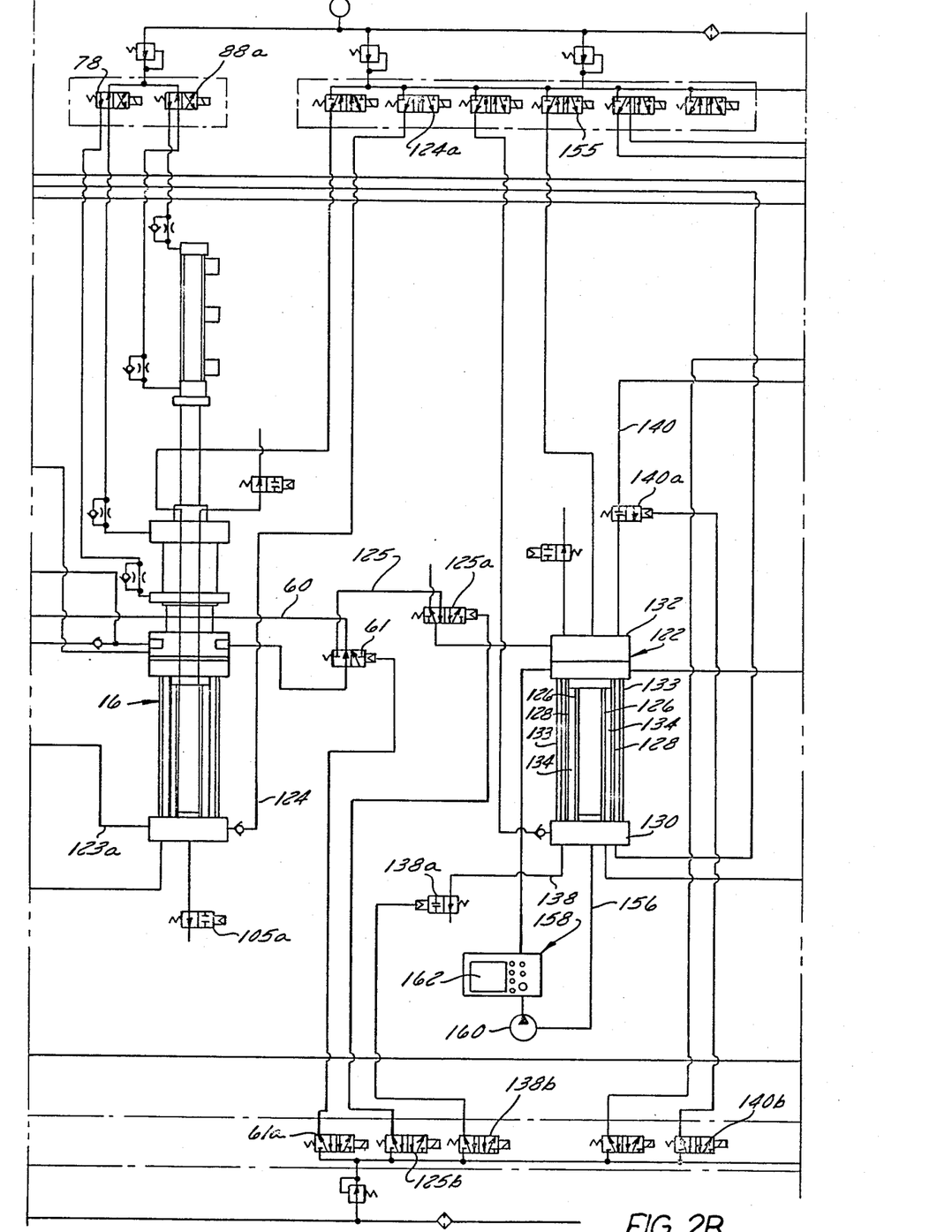
Figure 2C:
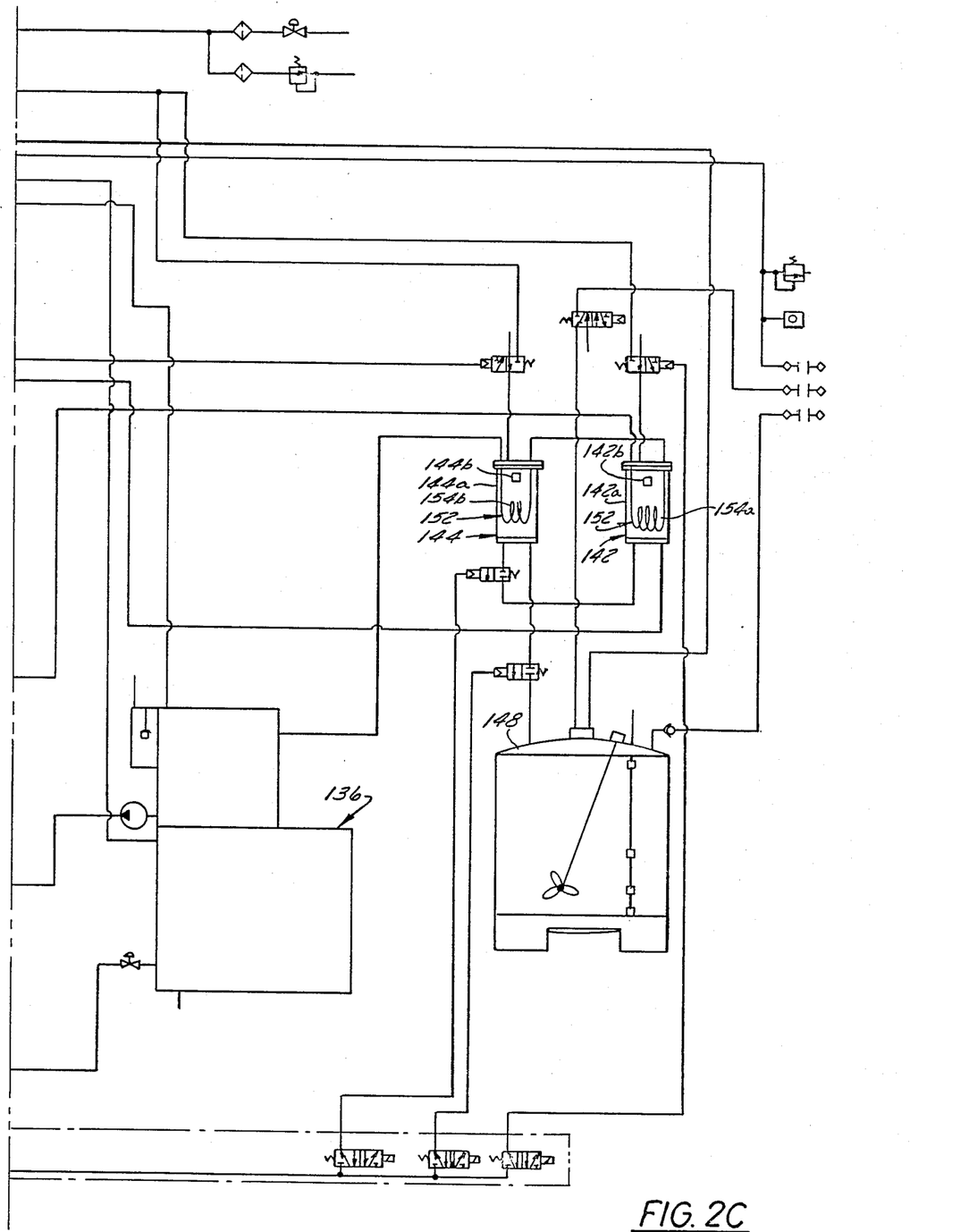

Generally, as shown in FIG. 1, the apparatus 10 may be mounted in a cabinet 11 which is in turn mounted on casters 12, so that the apparatus is as self-contained as possible and to provide some measure of portability. Referring now to FIGS. 2A, 2B and 2C, in the most preferred embodiment, the apparatus 10 includes a dilution tank 13 into which is added a sample of pulp slurry taken directly from the stock lines of a digester (not shown). A rough approximation of the consistency of the sample is generally known in advance by the operator taking the sample. The sample is then diluted by the addition of water from a source 14 of tap water, via a dilution water source valve 14a, until a consistency range of about 0.1% to about 0.5%, depending on pulp species, and preferably about 0.2%, is reached in the dilution tank 13. The diluted pulp is then, on command of the operator, introduced into a consistency testing chamber 16 by a circulation/sample valve 17, in turn controlled by a circulation/sample control valve 17a.

Consistency Testing Chamber

The preferred embodiment of the consistency testing chamber 16 is disclosed in detail in U.S. patent application Ser. No. 944,201, filed Dec. 22, 1986, wherein the relevant portion is referred to as the reaction chamber 16. That disclosure is incorporated in full herein by reference.

Figure 3:
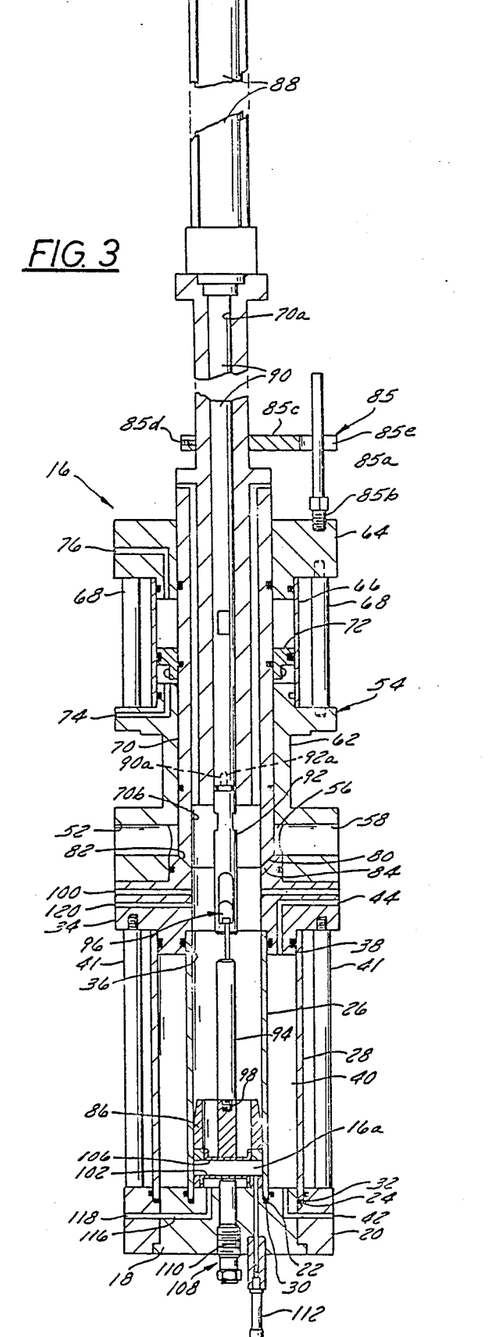
FIG. 3 is a plan view, partially in cross-section, of a cylinder to used in the apparatus shown schematically in FIGS. 2A, 2B and 2C, with the piston in the lowered position.

As can be seen in more detail by reference to FIG. 3, the consistency testing chamber 16 includes, at the bottom thereof, a header core 18 and header ring 20. When assembled together as there shown, inner and outer annular grooves 22 and 24 respectively are produced, concentric with each other. Into at least inner groove 22 is inserted an inner cylindrical wall 26. An O-ring 30 or other sealing and shock absorbing means may be placed at the bottom of the groove 22 for sealing purposes prior to assembly of the wall 26 into the groove. If a water jacket is desired, an outer cylindrical wall 28 would similarly be inserted into outer groove 24, with an O-ring 32 or other sealing and shock absorbing means placed at the bottom thereof. The water jacket would then exist in the enclosed annular space 40 between the walls 26 and 28. An upper header 34, having an inner axial bore 36 and a lower outer surface 38, is similarly mounted at the top of the cylindrical wall 26, and wall 28 if a water jacket is to be employed. Preferably the upper header 34 is attached to the header ring 20 by siitable removable means such as tie rods 41 threaded into tapped holes in upper of header 34 and header with screws in lower at locations outside of the cylindrical wall 28. The purpose of the water jacket would be to control the temperature of the consistency testing chamber 16 and maintain it at a predetermined temperature level. While temperature maintenance may not be critical for most consistency testing purposes, there may be situations where it would be important. A water jacket inlet 42 is thus provided in lower header ring 20 and header core 18 and a water jacket outlet 44 in upper header 34 for the circulation of hot water or other temperature-regulating fluid. The consistency testing chamber 16 is thus formed by header core 18 and header ring 20 at the bottom, inner cylindrical wall 26 and upper header 34 at the top.

Generally, the diluted pulp within the dilution tank 13 is continuously circulated by a stock pump 46 (FIG. 2A) from the dilution tank, via a supply line 48, controlled by a circulation/sample valve 17 as noted above, and via a transverse bore 52 (FIG. 3) in a chamber valve body 54 mounted on the upper header 34. From there the diluted pulp circulates to an annular opening 56 above and concentric with the top of the upper header 34 and communicating with transverse bore 52. The diluted pulp then exits via another transverse bore 58, which also communicates with annular opening 56, and finally returns to the dilution tank 13 via return line 60 and return line valve 61, in turn controlled by return control valve 61a. Preferably chamber valve body 54 includes a combination lower ring—valve body 62 separated from an upper ring 64 by a cylindrical housing 66. Ring-body 62 is preferably attached to upper ring 64 by tie rods 68 threaded into tapped holes in ring 64 and with screws in body 62 outside of housing 66. Closely fitted in sealing relation within chamber valve body 54 is a valve rod 70, which is moved axially within body 54 by means of an annular valve actuator piston 72. This valve actuator piston 72 is secured to the outer wall of the valve rod 70 and sealingly fitted within housing 66. A lower compressed air aperture 74 is provided in ring-body 62, and a corresponding upper compressed air aperture 76 in upper ring 64, communicating with a control valve 78 (FIG. 2A) to cause the axial movement of the valve rod 70. This axial movement causes the distal end 80 of valve rod 70, having a beveled outer edge and acting as a valve member, to move away from and toward engagement with a valve seat 82 formed by a beveled axial bore in the upper header 34, which bore communicates with the consistency testing chamber 16 just below. The travel of the valve actuator piston 72 is thus the distance between opposing faces of the ring-body 62 and the upper ring 64. The valve 84 thus formed by valve seat 82, valve rod 70 and ring-body 62 is thus opened and closed respectively thereby. Opening this valve is the first step in initiating a test cycle.

Since the valve rod 70 will have a natural tendency to rotate during the axial movement, anti-rotational means 85 are provided to prevent this rotation, since control and supply devices may generally be assumed to be attached to valve rod 70. In the preferred embodiment, this anti-rotational means 85 includes a rod 85a attached parallel to the direction of movement of the valve rod 70, such as by threaded fastener means 85b to the upper face of upper ring 64. A bracket 85c is non-rotatably attached to rod 70 by any suitable means such as a set screw 85d. This bracket 85c extends transversely toward rod 85a and has an aperture 85e at the end thereof into which rod 85a loosely slidably fits. This arrangement effectively prevents valve rod 70 from rotating with respect to the chamber valve body 54.

Figure 4:
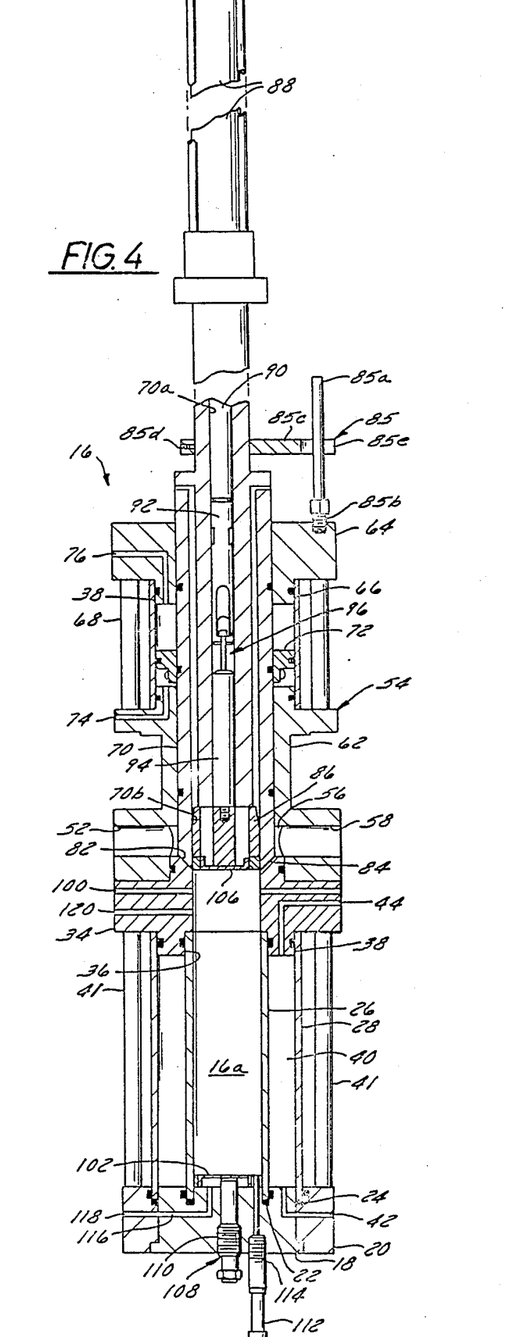
FIG. 4 is a view of the cylinder similar to FIG. 3, except with the piston moved to the raised position.

Before a pulp sample can be brought into the consistency testing chamber 16, however, a chamber piston 86, which is slidable axially within the chamber 16 and closely fitted therein, must be moved out of the chamber, as shown in FIG. 4. This removal is accomplished by a second power cylinder 88, controlled by second power cylinder control valve 88a (FIG. 2B). The rod end of cylinder 88 is attached coaxially at the top end of valve rod 70, and the blind end extends axially away therefrom. Valve rod 70 is bored at 70a, and a cylinder rod 90 of second power cylinder 88 passes through bore 70a. A rod extension 92 is connected to the distal end of the cylinder rod 90 by any suitable means such as having a threaded end 92a threaded into a tapped hole 90a formed axially in the end of rod 90. The distal end of the rod extension 92 is connected to a chamber piston rod 94 by means of a lost motion connection 96. The structure and significance of this lost motion connection 96, as well as the purpose and function of the chamber piston 86, will be explained more fully subsequently. Finally the distal end of the chamber piston rod 94 is connected to the chamber piston 86 by any suitable means such as a threaded fastening means 98. The lengths of the cylinder rod 90, extension rod 92, chamber piston rod 94 and consistency testing chamber 16 are determined so that, when the cylinder rod 90 is extended fully, the chamber piston 86 reaches the bottom of the chamber 16 with the lost motion connection 96 causing a small amount of lost motion. When the cylinder rod 90 is fully retracted into the second cylinder 88, on the other hand, as shown in FIG. 4, the chamber piston 86 is drawn axially completely out of the chamber 16 and into a recess 70b provided for that purpose in the distal end 80 of the valve rod 70.

Figure 5:
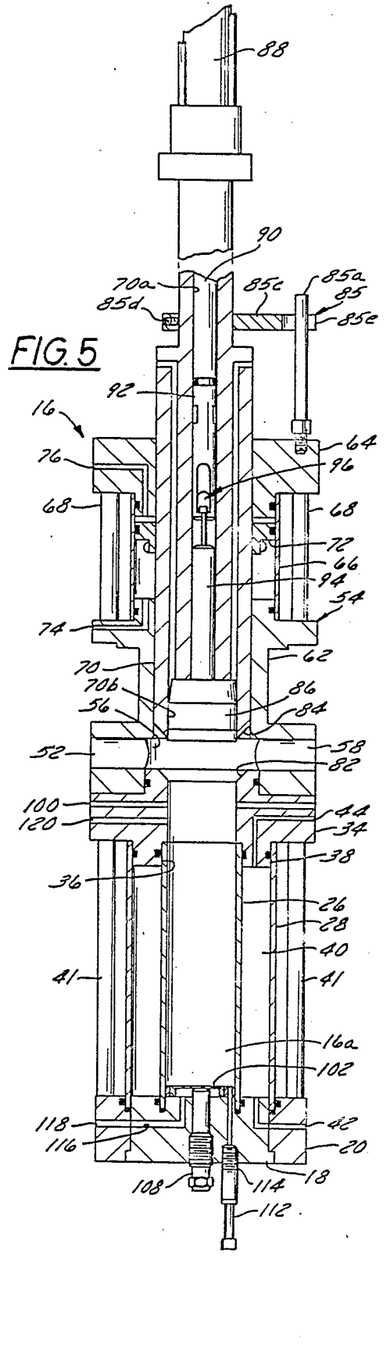
FIG. 5 is a view of the cylinder similar to FIG. 3, except with the main pulp stock inlet valve thereof in its open position.
Figure 6:
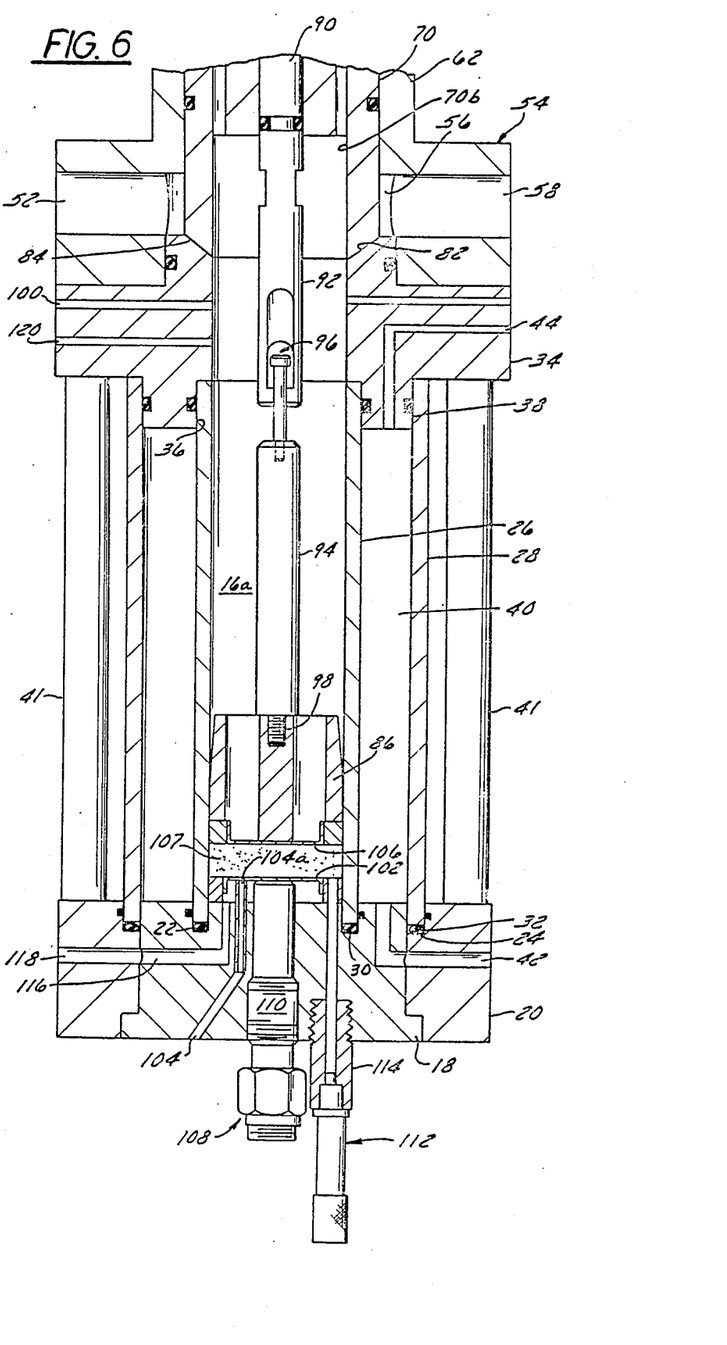
FIG. 6 is an enlarged view of the bottom portion of the cylinder shown in FIG. 3, to show the detail thereof, having the piston in its lowered position.

Having had the chamber piston 86 retracted, the consistency testing chamber 16 is ready to receive a pulp sample and begin a testing cycle. Referring now to FIGS. 5 and 6, to begin the testing cycle, tap water is allowed into the consistency chamber 16 through a water passage 100, until the water level has reached the level of a stationary screen 102 located at the bottom of the chamber. A separate drain passage 104 (FIG. 6) is provided for this purpose, with its inlet 104a positioned at the level of the screen 102. Accordingly, when valve 84 is opened as shown in FIG. 5 and as explained above to allow the diluted pulp to be charged into the chamber 16 from the supply line 48 (FIG. 2A), pulp does not build up on the screen. The consistency testing chamber 16 fills in a short time and the valve 84 is then closed, the position in FIG. 4 being resumed.

Testing the Consistency of the Sample

The first step in the testing cycle then is to determine the exact consistency of the pulp sample in the consistency testing chamber 16. While the approximate consistency is already known, as indicated above, from general knowledge of the consistency of the stock in the digester together with the known amount of water added to the stock sample in the dilution tank 13, it is important to know the exact consistency of the pulp sample in the chamber 16 to obtain accurate results. A preferred method of testing for consistency is disclosed generally in Kesler, U.S. Pat. No. 3,838,594, the disclosure of which is incorporated herein by reference.

In the present invention this method is carried out as follows. After the consistency testing chamber 16 is charged with a sample as described above and the valve 84 closes, the parts of the chamber 16 are again in the position shown in FIG. 4, with the chamber piston 86 fully retracted within the recess 70b in distal end 80 of the valve rod 70. At this point a settling supply valve 105 (FIG. 2A) is opened, consistency drain valve 105a (FIG. 2B) is opened, and water is allowed to flow through the consistency testing chamber 16 from top to bottom. This has the effect of speeding up the process of the pulp sample settling to the bottom of the chamber 16, on the screen 102. After a predetermined length of time, this settling flow is turned off and the second power cylinder 88 is energized, causing the chamber piston 86 to move downward. As referred to above, the chamber piston 86 is fitted closely within inner cylindrical wall 26, in sealing engagement therewith. The lower face of the chamber piston 86 is mostly foraminous, preferably having a chamber piston screen 106 affixed thereto. The apertures of chamber piston screen 106 are sized, as are the apertures of screen 102 at the bottom of the chamber 16, so as to allow the fluid in which the pulp is suspended to pass therethrough, while confining the pulp itself below the screen 106. Thus as chamber piston 86 moves downward the pulp of the sample is confined between the screens at the bottom of the chamber 16, while the liquid in the sample is allowed to remain in the chamber, above the chamber piston. Cylinder 88 is actuated slowly so as not to use up all of the lost motion connection 96, which in turn results in the sample being compressed between screen 102 and chamber piston screen 106 solely by the weight of the chamber piston 86 and chamber piston rod 94, which weight is a previously determined and constant quantity. The result of this compression is a pad 107 of a thickness determined by the pressure applied and the volume of material contained in the pad. After a predetermined length of time compressing the sample, the position shown in FIG. 6 is reached, and the thickness of the pad is measured by a measuring means 108.

In the preferred embodiment, this measuring means 108 includes a transducer 110 which may preferably be connected to an electronic computer means 111 (FIG. 1) for calculating, storing and later retrieving, as needed, the consistency of the pulp sample from a reference curve manually determined by use of the consistency testing chamber 16 employing principles disclosed in the Kesler patent referred to above. Preferably, to give the most accurate reading, this transducer 110 is installed axially through the bottom of the header core 18, with the top of the transducer touching the screen 102. For the transducer to work properly, then, the header core 18 and the micrometer screw 114 must be constructed of a non-magnetic, non metal material that stands up well to corrosive reagents, such as polysulfone, PVC type 1 or Teflon TFE. The screen 102 must also be non-magnetic and corrosion-resistant. The material of the chamber piston 86 must also be corrosion-resistant but the piston must be ferrous, at least to an extent. Stainless steel is the preferred material. The transducer 110 then senses the distance between the screens 102 and 106 by sensing the distance between itself and the ferrous chamber piston 86. A calibration means 112 is provided to allow calibration of the measuring means 108. To this end, a micrometer screw 114 is provided which can accurately measure the distance between the screens 102 and 106 when no pad 107 is in place, that is, when there is no test in progress. Once again this micrometer screw 114 is preferably inserted axially through the header core 18 parallel to but spaced apart from the transducer 110, and exits the upper surface of the header core 18 alongside the screen 102 or through an aperture provided for that purpose therein. Then, when it is desired to calibrate the measuring means 108, the micrometer is set at a predetermined level at which the calibration is desired and the chamber piston 86 lowered into contact with it. The measuring means is then adjusted accordingly. The micrometer is then withdrawn from the chamber to its storage position as shown in FIG. 6.

Testing for Transmittance

After the consistency of the sample has been determined, the pad 107 must be disintegrated for transfer to a reaction chamber 122, where a chemical reaction will be conducted to determine the volume of lignin or other relevant substances are in the sample. To accomplish this disintegration, the chamber piston 86 is again retracted, returning to the position shown in FIG. 4, with the liquid which carried the pulp sample into the testing chamber 16 still present in the chamber. An amount of the liquid is drained from the chamber 16 such as via drain outlets 116 and 118 to a drainage measuring chamber 123 (FIG. 2A) to lower the level of the liquid in the chamber 16 by a predetermined amount. Air is then introduced into the chamber 16 at the bottom thereof, via an air inlet 124 (FIG. 2B), to agitate the liquid and break up the pad 107, by bubbling up through the chamber. Valve 84 (FIG. 5) is opened to allow the transfer of liquid pulp sample via transfer bore 58 thru transfer line 125.

Referring now to FIGS. 2A, 2B and 2C, once this breakup is accomplished, the (again liquid) pulp sample is carried out of the consistency testing chamber 16 into the reaction chamber 122 via a transfer line 125, controlled by a transfer valve 125a, in turn actuated by a transfer control valve 125b. The necessary medium to transfer the pulp sample may be supplied by water from a hot water source 136, via a sample transfer valve 125c. The preferred procedure is as follows. Circulation/sample valve 17 is switched from directing flow toward consistency testing chamber 16 to directing flow back toward the dilution tank 13. At the same time, return line valve 61 is switched from directing flow back toward the dilution tank 13 to directing flow toward the reaction chamber 122 and transfer valve 125a is opened. Then when sample transfer valve 125c is opened, water is allowed to flow into the bottom of the consistency testing chamber 16, forcing the sample upward and out of chamber 16 and into reaction chamber 122. In addition, an inlet flush valve 125d is opened, allowing tap water to flow into transverse bore 52 and annular opening 56, and out via transverse bore 58 of the consistency testing chamber 16, to flush that portion of the chamber thereby ensuring transfer of all of the sample to the reaction chamber 122. Reaction chamber drain valve 138a will generally be opened during this transfer to allow the expected excess transfer fluid to escape by that route.

The reaction chamber 122 is constructed similarly to the consistency testing chamber 16 with the exception that no pistons, power cylinders or position sensors are necessary. The reaction chamber 122, then, is constructed of an inner cylindrical wall 126, surrounded by an outer cylindrical wall 128, both mounted in concentric, inner and outer annular grooves formed both in a base 130 at their bottom and in a header 132 at their top. The base 130 and header 132 may be held together by any suitable means such as tie rods 133 secured lengthwise between them. The annular space 134 existing between the cylindrical walls 126 and 128 is filled with heated liquid such as water from water heater 136. The space 134 thus acts as a temperature regulator or water jacket to control the temperature of the reaction chamber 122.

Once the pulp sample is transferred to the reaction chamber 122, the liquid of the sample is drained from the chamber via a drain opening at the bottom thereof communicating with a drain line 138, controlled by a drain valve 138a, which is in turn actuated by a drain control valve 138b. Once the liquid is completely drained, by a method to be explained subsequently, drain valve 138a is closed and a reagent is added to the pulp via a reagent inlet in header 132 communicating with a reagent line 140. As indicated in FIGS. 2B and 2C, reagent line 140 has its source at a reagent measuring chamber 142, wherein an exact amount of reagent is measured and heated prior to addition of the reagent to the reaction chamber 122. The reagent measuring chamber 142 includes an enclosure 142a and means 142b for sensing the liquid level in the enclosure, such as a float switch. In one preferred embodiment, the reagent is preheated in a preheat chamber 144, similar to the reagent measuring chamber 142 including enclosure 144a and level sensing means 144b, before passing into the reagent measuring chamber itself for final measuring and heating. Then, when the reagent in reagent measuring chamber 142 is transferred to reaction chamber 122, the reagent in preheat chamber 144 is transferred to reagent measuring chamber 142. Preheat chamber 144 is then refilled with reagent from a reagent reservoir 148.

As indicated, both the reagent measuring chamber 142 and the preheat chamber 144 include means 152 for preheating the reagent contained therein. The purpose of this preheating means 152 is to ensure that the reagent enters the reaction chamber 122 at about the predetermined temperature established as optimum for reaction of the reagent with the lignin in the pulp sample and the temperature established for the water jacket of the chamber 122, so as not to unduly extend the length of time of the reaction occurring in the chamber. To accomplish this purpose, each preheating means 152 includes a coil 154 constructed of temperature conducting material and located within the respective reagent container, which coil communicates with a source of heated fluid. In particular, coil 154a, located in the reagent measuring chamber 142 receives its heated fluid from the outlet of the water jacket 134 surrounding the reaction chamber 122, while coil 154b, located in the preheat chamber 144, receives its heated fluid from the outlet of coil 554a. Thus in the embodiment shown the heated fluid circuit leads from the water heater 136 to the water jacket 134, then to coil 154a, on to coil 154b, and back to the water heater 136.

The reaction to be conducted in the reaction chamber 122 is an oxidation and breaking down of the fibers of the pulp sample, and a removal therefrom of the lignin. To this end, the preferred reagent is nitric acid. By experimentation it has been determined that the reagent is preferred to be in the range of five to twenty per cent nitric acid in water, and most preferredly 14% nitric acid. The reservoir 148 then contains that preferred nitric acid solution. To begin the reaction, the liquid used to transfer the sample pad 107 into the reaction chamber 122 is drained out via drain line 138 as indicated above. Low pressure air, such as from a dewatering valve 155, is employed to shorten the time required for this draining, and to dewater the sample to an extent. Next, the quantity of reagent measured by the reagent measuring chamber 142 is introduced into the reaction chamber 122 via reagent line 140 as referred to above. The mixture of pulp and reagent is then allowed to react until a peak level of light absorbance is reached by the reagent.

The level of light absorbance of the reagent is continuously monitored by means of a circulating loop 156 containing a means 158 for determining the light absorbance of a liquid. In the preferred embodiment the loop 156 includes a pump 160 for ensuring the continuous circulation of the reagent from the reaction chamber 122 through the loop. The means 158 preferably includes a flow cell colorimeter for determining the light absorbance of the reagent as it flows through the loop, as well as an output device 162 such as a strip recorder for recording the level of light absorbance of the reagent as the reaction progresses. After the peak absorbance has passed, the value of the peak is sent to the electronic computer means 111 for combination with the consistency previously determined to generate an index figure indicative of the amount of the lignin present in the sample before the reaction.

The length of time it takes to reach this peak depends upon the temperature at which the reaction is conducted and upon the type of wood from which the pulp was manufactured. Generally, however, the time interval is within the range from 3 minutes to 12 minutes. Of course shorter reaction times are desirable so that the total test cycle can be made as short as possible, allowing samples to be taken more often and the degree of cook more closely monitored. In addition, shorter test cycle times are further enabled by the fact that the consistency testing is done in a separate chamber from the chemical reaction, allowing the reaction to be conducted while the consistency of the next sample in order is concurrently being conducted.

As to the temperature at which the reaction is preferred to be carried out, generally, the reaction temperature is controlled by the water jacket temperature and in turn the temperature at which the water heater 136 maintains its water. These temperatures are generally maintained in the range from 80 to 95 degrees Celsius. Temperatures toward the higher end of that range cause faster reactions and allow the use of shorter time intervals, although there may be cases where it is desirable to slow the reaction to exert better monitoring and control thereover. In addition the preferred reaction time intervals for pulps manufactured from soft woods range from 4 to 6 minutes, while for hard woods the intervals range from 7 to 10 minutes.

After the peak absorbance value has been observed and recorded, the reagent and sample are drained from the reaction chamber 122 and the chamber is readied for the introduction of another sample. Generally it will be preferred to flush the reaction chamber 122 with water from hot water source 136. A heated flush is preferred to avoid the delay which could be caused by having to bring the reaction chamber back up to the desired temperature before beginning the next test cycle therein.

While the apparatus hereinbefore described is effectively adapted to fulfill the aforesaid objects, it is to be understood that the invention is not intended to be limited to the particular preferred embodiments of on-line apparatus and method for determining the degree of completion of pulp cook herein set forth. Rather, it is to be taken as including all reasonable equivalents without departing from the scope of the appended claims.

What is claimed as the invention is:

1. An apparatus for analyzing pulp stock, including wood pulp and water to determine the amount of cooking to which said pulp has been subjected, comprising:

means for diluting a sample of said pulp stock;

consistency testing means for receiving said sample from said diluting means and determining the consistency of said sample;

reaction chamber means for holding said sample in preparation for and during a chemical reaction;

transfer means connected between said reaction chamber means and said consistency testing means for transferring said sample from said consistency testing means to said reaction chamber means;

reagent control means connected to said reaction chamber means for adding reagents to said pulp sample while in said chamber means and for draining off said reagents from said pulp sample;

monitoring means connected to said reaction chamber for continuously monitoring said reagents within said reaction chamber, for continuously examining said reagents, for continuously determining the light absorbance of said reagents during said chemical reaction, and further comprising means for determining a maximum light absorbance exhibited by said reagents, and means for terminating said reaction upon said reagents reaching said maximum light absorbance;

wherein said examining and determining means include a flow cell colorimeter connected to said reaction chamber via circulating loop means such that said reagents flow from said reaction chamber through said circulating loop means and return to said reaction chamber.

2. An apparatus as recited in claim 1 wherein said consistency testing means includes:

consistency testing chamber means for containing said sample;

compressing means for compressing said sample along a predetermined direction within said consistency testing chamber to a predetermined pressure; and measuring means for measuring said compressed sample along said predetermined direction.

3. An apparatus as recited in claim 1 further comprising means for maintaining the temperature of said reaction chamber means at a predetermined temperature throughout the time the reagents are in said reaction chamber means.

4. An apparatus as recited in claim 2 wherein said consistency testing chamber includes at a screen end thereof a screen of non-magnetic material, wherein said compressing means includes a piston positioned within said consistency testing chamber for confining said pulp stock sample between itself and said screen end of said consistency testing chamber, and means for moving said piston toward said screen end of said consistency testing chamber, at least a portion of said piston comprising magnetic-type material, and wherein said measuring means includes transducer means positioned within said consistency testing chamber just on the opposite side of said screen from said sample, for sensing the distance between said screen and said piston.

5. An apparatus as recited in claim 4 wherein said mesauring means further includes calibration means, including micrometer means inserted through said screen end of said consistency testing chamber, for testing said transducer means and ensuring the accuracy thereof.

6. A method for continuously analyzing pulp stock, including wood pulp and water, in a pulp digester, to determine the amount of cooking to which said pulp has been subjected, comprising the steps of:

diluting a sample of said pulp stock from said digester to an approximately known range of consistency;

determining the consistency of said pulp stock sample in a consistency testing chamber;

transferring said pulp stock sample to a reaction chamber;

adding a reagent to said reaction chamber and allowing said reagent to react with said pulp stock sample at a predetermined temperature;

continuously monitoring the light absorbance of said reagent during the reaction, said light absorbance being determined by the amount of cooking to which said pulp has been subjected, the current length of time that said reagents have been reacting with said pulp stock sample, and the consistency of said sample, the peak light absorbance being the highest value of light absorbance of said reagents observed during the reaction;

determining the amount of cooking from a known relationship thereof to the peak light absorbance of said reagent and the consistency of said sample; and terminating the reaction after said peak light absorbance has been reached.

7. A method as recited in claim 6 wherein determining said consistency of said sample includes:

containing said sample in said consistency testing chamber;

compressing said sample along a predetermined direction to a predetermined pressure;

measuring said compressed sample along said predetermined direction; and determining the consistency of said compressed sample from a known relationship thereof to the measurement of said sample along said predetermined direction.

* * * * *